United States Patent [19]

Inouye et al.

[11] 4,327,072
[45] Apr. 27, 1982

[54] TYROSYLATED PROINSULIN C-PEPTIDE DERIVATIVES

[75] Inventors: Ken Inouye, Kobe; Masao Kono, Ibaraki; Nobuo Yoshida, Nishinomiya; Masuhisa Nakamura, Toyonaka; Tadashi Okabayashi, Nishinomiya; Ken'ichi Igano, Nara, all of Japan

[73] Assignee: Shionogi & Co., Ltd., Osaka, Japan

[21] Appl. No.: 97,671

[22] Filed: Nov. 27, 1979

[51] Int. Cl.³ .................. G01N 33/56; A61K 43/00; C07C 103/52
[52] U.S. Cl. ......................... 424/1; 23/230 B; 260/112.5 R; 424/12
[58] Field of Search .................. 424/1, 1.5, 12; 23/230 B; 260/112.5 R

[56] References Cited

FOREIGN PATENT DOCUMENTS 1464630 2/1977 United Kingdom .

OTHER PUBLICATIONS

Kuzuya, Chem. Abstracts, vol. 88, No. 7, Feb. 13, 1978, #47135e.

Heding, Chem. Abstracts, vol. 88, No. 3, Jan. 16, 1978, #18589a.

Nakazawa et al., Chem. Abstracts, vol. 88, No. 1, Jan. 2, 1978, #2641a.

Melani et al., Identification of Proinsulin and C-Peptide in Human Serum by Specific Immunoassay, Proc. Natl. Acad. Sci. U.S. 67,148 (1970).

*Primary Examiner*—Christine M. Nucker
*Attorney, Agent, or Firm*—Birch, Stewart, Kolasch & Birch

[57] ABSTRACT

The disclosed peptide derivative of the formula:

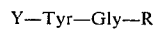

Y—Tyr—Gly—R

Wherein, Y represents a hydrogen atom or an amino protecting group, Tyr represents a tyrosine residue wherein at least one of the hydrogen atoms on the phenyl ring may be substituted by a radioactive iodine, Gly represents a glycine residue, and R represents a peptide residue corresponding to an amino acid sequence which includes at least positions 7 through 21 of human proinsulin C-peptide proves to be useful for determining C-peptide level in human serum.

9 Claims, 1 Drawing Figure

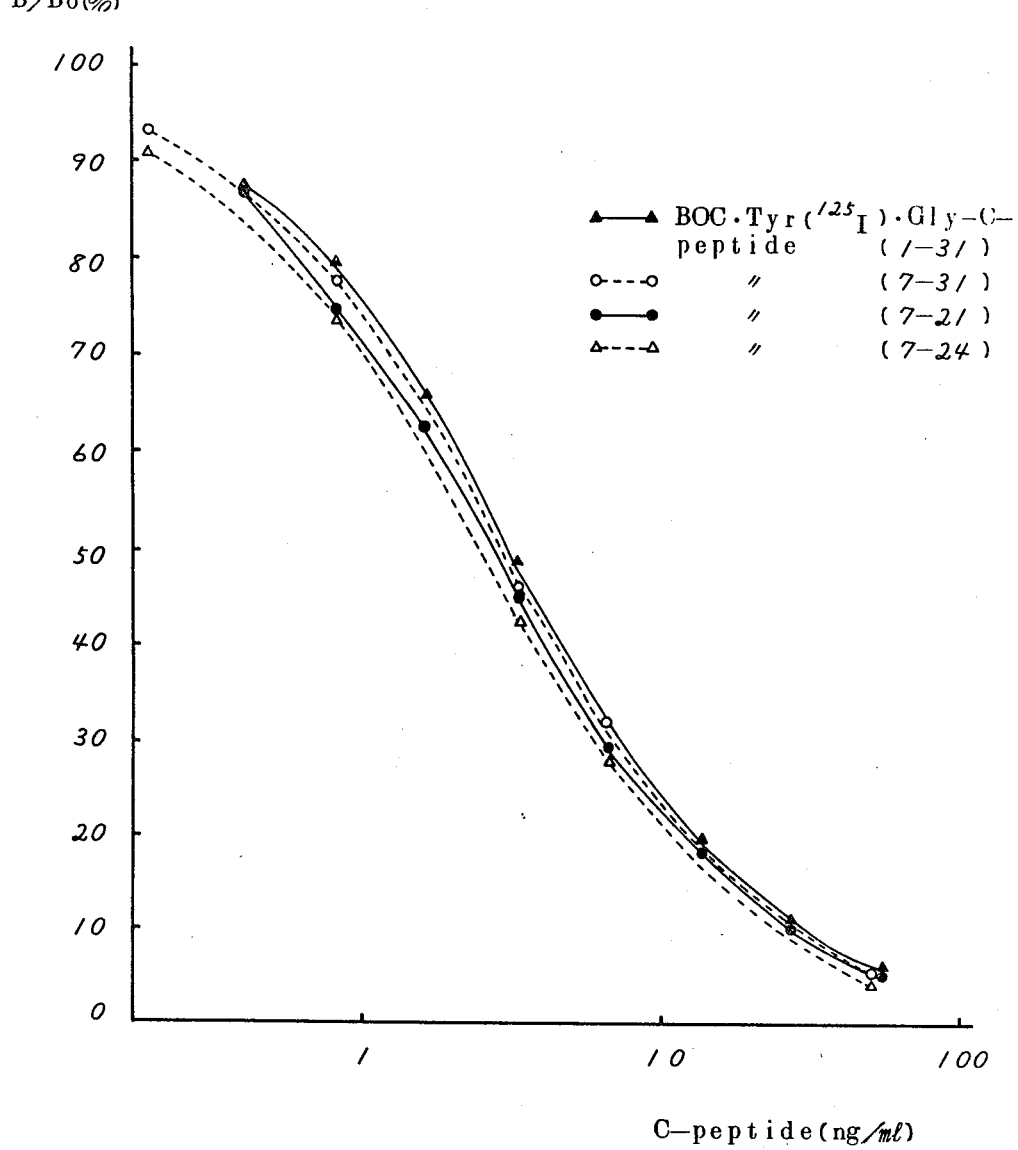

TYROSYLATED PROINSULIN C-PEPTIDE DERIVATIVES

BACKGROUND OF THE INVENTION

1. Field of the Invention

The present invention relates to the derivatives of human C-peptide and its fragments (short-chain analogues) useful for the determination of proinsulin C-peptide level in human serum.

In the radioimmunoassay performed for evaluating the function of pacreatic β-cell, it is an accepted and prevalent notion that the measurement of C-peptide in serum is more reliable in a practical point of view than that of insulin itself in serum, and a number of investigations in connection with this notion have hithertofore been reported (See, for instance, Kaneko; Taisha 10, 1288 (1973), and Saishin-igaku 31, 839 (1976)).

The ground of this notion appeared in these papers may be summarized as follows:

(1) It is difficult to measure accurately the concentration of insulin itself in serum of diabetics who have been or are being treated with insulin, because they hold a naturally occurring antibody against insulin.

(ii) The half-life of insulin in human vascular (vein) is limited to as short as 3-4 minutes whereas that of C-peptide is as long as about 13 minutes, and (iii) C-Peptide is a peptide which connects the A and B chains of insulin together to constitute the proinsulin molecule and is to be liberated along with an equimolar amount of insulin simultaneously in accordance with the decomposition of proinsulin in pancreatic β-cells.

C-peptide herein referred to is a peptide composed of 31 amino acid residues which correspond to positions 33–63 of human proinsulin, but it has no tyrosine residue. Therefore, C-peptide can not be labeled, as it stands, with radioactive iodine for performing radioimmunoassay.

2. Description of the Prior Art

Steiner and others have therefore proposed the use of an N-tyrosylated C-peptide, the tyrosine residue of which may be labeled with radioactive iodine (Steiner, D. F. et. al.: Proc. Natl. Acad. Sci. U.S., 57, 473 (1967)).

Steiner's tyrosylated C-peptide is regarded as being prepared according to the method described by Melani et. al. (Melani, F. et. al., Proc. Natl. Acad. Sci. U.S., 67, 148 (1970)).

According to this method, the C-peptide may be tyrosylated at pH 7.6 with the N-carboxy anhydride of tyrosine, that is:

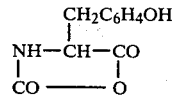

In this method, however, it is unable to stop the reaction at a predetermined step and, therefore, the concommitant formation of C-peptide derivatives having more than one tyrosines is inevitable.

That is, the product thus obtained is not a single substance but a mixture of C-peptide derivatives, in which one or more tyrosine residues are introduced. The ratios of the components may vary from one lot to another and their separation would be virtually impossible.

Although Steiner contends that the biological activity such as antibody specificity might scarcely be affected by the poly-tyrosylation, it is difficult to affirm his contention in every and all respects.

In general, the introduction of tyrosine residue into a certain peptide may be carried out with one of the following compounds as acylating agent:

Z-Tyr(Z)-X (i)

Z-Tyr(Bu$^t$)-X (ii)

Z-Tyr-X (iii)

wherein Z represents the benzyloxycarbonyl group, X represents an active group such as Oxysuccinimidyloxy, trichlorophenoxy or azide group and Bu$^t$ represents the tertiary butyl group, and wherein Z may be replaced by Boc (tertiary butoxycarbonyl group) and Bu$^t$ may be replaced by Bzl (benzyl group) in either case. The following paragraphs will describe the use of these compounds for tyrosylation of C-peptide.

A method which employs the agent (i) is disclosed in the specification of Japanese unexamined Pat. No. 25,767/77 and one which utilizes the agent (ii) is reported by Naithani and others (Naithani, V. K., et. al., Hoppe Seyler's Z. Physiol. Chem., 356, 1305 (1975)). In these cases, however, the protecting group on the side chain hydroxyl group of tyrosine has to be removed prior to the labeling.

Thus, the acylation product is subjected to catalytic hydrogenolysis or acidolysis with hydrogen fluoride and the like in the former case, and to acidolysis with trifluoroacetic acid (TFA) (for removal of Bu$^t$) or hydrogen fluoride (for removal of both Bu$^t$ and Z) in the latter case.

The catalytic hydrogenolysis may be applied to a short chain peptide but hardly applicable to a long chain peptide, because of its low reaction rate. (See: for instance, V. K. Naithani et. al. ibid).

If the acidolytic deprotection is employed, the resultant tyrosine residue tends to undergo modification by the possible action of liberated carbonium cation. Furthermore one can not exclude the possibility that the other part of the C-peptide molecule would undergo modification simultaneously upon acid treatment.

In such cases as those mentioned above, the purification of the product by means of fractionation or the like would present considerable difficulties.

By employing the agent (iii) the above mentioned drawback may be avoided, but the acylation of C-peptide must be done with an excess amount of the reagent to complete reaction. As a result, possible overacylation at the side chain of tyrosine may not be avoided.

The only case in which the overacylation does not occur is when X=N$_3$ in (iii). However, the tyrosine azide generally has tendency to form an inactive amide in the presence of water during the course of its preparation.

Under the circumstances, the specifications of Japanese Pat. No. 10,872/77 and Japanese Unexamined Pat. No. have proposed the exploitation of a newly defined "C-peptide" which is unique in a sense that it is a derivative of the C-peptide defined by Steiner (a peptide with a sequence of 31 amino acid residues corresponding to positions 33–63 of human proinsulin) and embodies extra sequences Arg-Arg (arginyl-arginine) and Lys(-For)-Arg-OH (N$^ε$-formyllsylarginine) at the N— and C—terminal positions, respectively, of C-peptide.

This hexatriacontapeptide contains amino acid residues corresponding to positions 31-65 of human proinsulin and has a tyrosine residue at the N-terminal. The hydroxyphenyl group of tyrosine may be labeled with $^{125}I$.

They used this hexatriacontapeptide as antigen in place of C-peptide itself, because the latter had been reported to be only weakly antigenic even in the form of an albumin bound conjugate.

However, the proposed method has a disadvantage in the synthesis of antigen, as it requires operation for coupling 35 amino acid residues as compared to 31 of the normal human C-peptide. The extention of the C-peptide sequence by the four additional residues is deemed to be not necessarily essential for the introduction of the tyrosine residue.

SUMMARY OF THE INVENTION

It is therefore the primary object of the present invention to provide a novel tyrosylated proinsulin C-peptide derivative which overcomes the aforementioned drawbacks and obviates inconvenience inherent to the prior arts.

It is another object of the present invention to provide such a tyrosylated C-peptide derivative of simpler structure.

It is a further object of the present invention to provide a derivative which can be prepared easier than the prior art derivatives.

It is a still other object of the present invention to provide a derivative of improved stability in use and at storage.

It is still further object of the present invention to provide an agent for the determination of C-peptide level in human serum by means of radioimmunoassay.

According to the present invention there is provided a tyrosylated proinsulin C-peptide derivative of the formula:

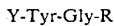

wherein, Y represents a hydrogen atom or an amino protecting group, Tyr represents a tyrosine residue wherein at least one of the hydrogen atoms on the phenyl ring may be substituted by a radioactive iodine, Gly represents a glycine residue, and R represents a peptide residue corresponding to an amino acid sequence which includes at least positions 7 through 21 of human C-peptide.

The entire amino acid sequence of the stated derivative can be illustrated with numerals representing the positions in the C-peptide molecules as:

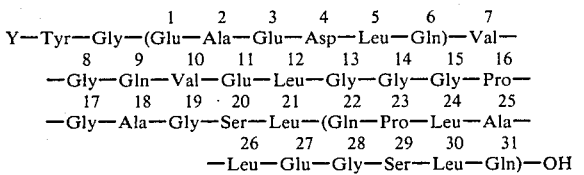

wherein, Y and Tyr are having the same significance as previously mentioned and the amino acid residues in the parentheses may optionally and fully or partially be omitted. A reason for the insertion of a glycine residue between the tyrosine residue and the rest of the amino acid sequence is to overcome the previously stated difficulty inherent to the use of tyrosine azide or, at least, to reduce the inconvenience related thereto.

Glycine is deemed to be more adequate for the above purpose than other amino acids, because the former has no side chain, so that the possible danger of racemization is fully eliminated.

Any amino protecting groups may be used as Y, but the tertiary butoxycarbonyl group is particularly preferred. The reason for this is that the selective removal of the side chain protecting group of the tyrosine residue must be done in the synthesis of Z-Tyr(Bu$^t$)-Gly-OMe or Boc-Tyr(Bzl)-Gly-OMe, an intermediate for Y-Tyr-Gly-N$_3$, and that N-Boc-O-Bzl-tyrosine is more easily available as starting material than N-Z-O-Bu$^t$-tyrosine. In addition to this, the Boc group is more hydrophilic than the Z group and is less liable to decrease the solubility of Y-Tyr-Gly-C-peptide.

Although the derivatives of C-peptide and its short-chain analogues proposed in the present invention are of simpler structure, each of them performs function comparable to the tyrosylated C-peptide derivative currently in use and has a superior stability by virtue of the presence of the amino protecting group Y so that it may be kept intact during the whole assaying procedure. It is needless to say that the tyrosylated C-peptide and short-chain analogues of simpler structure are advantageous in synthetic point of view over the compounds currently being used.

DESCRIPTION OF THE PREFERRED EMBODIMENT

The disclosed derivatives may be obtained by simply contacting the previously prepared azide [Boc-Tyr-Gly-N$_3$] with a synthetic peptide corresponding to an amino acid sequence including at least positions 7 through 21 of the human C-peptide, and the process therefor will be illustrated in more detail referring to the preparation described in the following paragraphs.

Preparation

Process (1), Boc-Tyr(Bzl)-Gly-OMe

Boc-Tyr(Bzl)-OH (2.79 g, 7.5 mmol) and tri-n-butyl amine (1.79 ml, 7.5 mmol) are dissolved in methylene chloride (15 ml) and to this is added H-Gly-OMe.HCl (0.94 g, 7.5 mmol). The mixture is cooled in ice and dicyclohexylcarbodiimide (1.55 g, 7.5 mmol) is added with methylene chloride (5 ml) as solvent. The mixture is allowed to stand overnight at 4° C. After the crystalline precipitates of dicyclohexylurea has been filtered off, the solvent is evaporated in vacuo. The resultant residue is redissolved in ethyl acetate and the solution is washed with ice-cold 1 M hydrochloric acid, water and 1 M sodium hydrogencarbonate, successively.

After being dried over anhydrous magnesium sulfate, this solution is evaporated to dryness in vacuo. Recrystallization of the crystalline residue from ethyl acetate-diethylether affords the title compound (2.72 g, 82%).
mp 121°–122° C., $[\alpha]_D^{23} + 1.8 \pm 0.4°$ (c 1.0, MeOH).
Anal. Calcd for $C_{24}H_{30}N_2O_6$: C, 65.14; H, 6.83; N, 6.33%. Found: C, 65.16; H, 6.85; N, 6.39%.

Process (2), Boc-Tyr-Gly-NHNH$_2$

Boc-Tyr(Bzl)-Gly-OMe (0.40 g), obtained above in Process (1), in methanol (Ca. 10 ml) containing acetic acid (0.5 ml) is hydrogenolyzed over palladium black for 6 hours. A syrupy residue obtained after the removal of catalyst by filtration and solvent by evaporation is dissolved in ethyl acetate and the solution is washed with water, dried over anhydrous magnesium sulfate and evaporated in vacuo. The resultant Boc-Tyr-Gly-OMe is dissolved in methanol (5 ml), hydrazine hydrate (0.22 ml) is added and the mixture is allowed to stand overnight at 25° C. The residue obtained upon evaporation of the solvent in vacuo is dissolved in water and the solution is, after saturation with sodium chloride, extracted with ethyl acetate. The extract is dried over anhydrous magnesium sulfate and evaporated to dryness. The crystalline residue is recrystallized from ethyl acetate to afford the title compound (0.29 g, 73%). This compound loses its crystalization solvent to become amorphous at 75°–85° C.

Anal. Calcd for $C_{16}H_{24}N_4O_5 \cdot CH_3CO_2C_2H_5$: C, 54.53; H, 7.32; N, 12.72%. Found: C, 54.42; H, 7.33; N, 13.23%.

Process (3), Boc-Tyr-Gly-$N_3$

The product obtained in accordance with Process (2) (26.4 mg, 60 μmol) is dissolved in dimethylformamide (DMF. 0.5 ml) and cooled down to $-15 \sim -20°$ C. To this solution are added 4 M hydrogen chloride/dioxane (0.06 ml) and isoamyl nitrite (8.7 μl, 6.6 μmol) successively, and the mixture is stirred for 10 minutes, cooled down to $-30 \sim -40°$ C., and then neutralized with diisopropylethylamine (DIEA, 39 μl, 300 μmol) to afford a solution of the title azide.

Process (4), Boc-Try-Gly- human C-peptide

Synthetic human C-peptide (20.2 mg, ca. 6 μmol) and DIEA (5 μl, 40 μmol) are dissolved in a mixture of DMF (0.5 ml) and water (0.3 ml). To this is added the azide solution obtained in Process 3) above and the mixture is allowed to stand at 4° C. for 18 hours. This is applied to a column (1.74×108 cm) of Sephadex G-25 (medium) (Registered trademark) which has been previously equilibrated with 0.05 M ammonium hydrogencarbonate, and the elution is performed with the same buffer. Fractions (3.75 ml/tube) are collected and those corresponding to the first peak (tubes 24–40), as monitored by absorption at 230 nm, are combined and lyophilized to afford the title compound (21.7 mg). Amino acid ratios in acid hydrolysate (theoretical values are given in parentheses):

| Asp, | 1.00 (1); | Ser, | 2.03 (2); | Glu, | 7.96 (8); |
| Pro, | 2.10 (2); | Gly, | 7.89 (8); | Ala, | 2.66 (3); |
| Val, | 2.04 (2); | Leu, | 6.00 (6); | Tyr, | 0.81 (1)*. |

*The Tyr content in intact peptide is 1.04 mole/mole peptide as measured spectrophotometrically at 290 nm in 0.1 M sodium hydroxide.

Process (4-1), Boc-Tyr-Gly- human C-peptide-(7-31), -(7-24) and -(7-21)

Synthetic human C-peptide (7-31)-pentacosapeptide, (10 mg, ca. 3.6 μmol) and DIEA (3 μl, 24 μmol) are dissolved in 0.4 ml of DMF. To this is added the azide solution obtained in Process 3) above from 36 μmol of the hydrazide and the mixture is allowed to stand at 4° C. for 2 days.

This is applied to a column (1.74×108 cm) of Sephadex G-25 (medium) which has previously equilibrated with 0.05 M ammonium hydrogen carbonate, and the elution is performed with the same buffer. Fractions (3.75 ml/tube) are collected and those corresponding to the first peak (tubes 22–26), as monitored by absorption at 230 nm, are combined and lyophilized to afford the title compound (11 mg).

Essentially the same procedure is followed respectively with human C-peptide-(7-24)-octadecapeptide and human C-peptide-(7-21)-pentadecapeptide, to obtain the corresponding compounds.

The compound derived from the octadecapeptide appeared in tubes 25–41, and the one from the pentadecapeptide appeared in tubes 26–43 in their column chromatography. Amino acid ratios in the acid hydrolysates (theoretical values are given in paretheses) of the peptides obtained above are:

| 1. Boc—Tyr—Gly—human C—peptide—(7-31) | | | | | |
|---|---|---|---|---|---|
| Ser, | 1.91 (2); | Glu, | 4.50 (5); | Pro, | 2.17 (2); |
| Gly, | 7.86 (8); | Ala, | 2.07 (2); | Val, | 1.64 (2); |
| Leu, | 5.00 (5); | Tyr, | 1.12 (1). | | |

| 2. Boc—Tyr—Gly—human C—peptide—(7-24) | | | | | |
|---|---|---|---|---|---|
| Ser, | 0.90 (1); | Glu, | 2.84 (3); | Pro, | 2.10 (2); |
| Gly, | 7.34 (7); | Ala, | 1.06 (1); | Val, | 1.91 (2); |
| Leu, | 3.00 (3); | Tyr, | 1.28 (1). | | |

| 3. Boc—Tyr—Gly—human C—peptide—(7-21) | | | | | |
|---|---|---|---|---|---|
| Ser, | 0.99 (1); | Glu, | 1.87 (2); | Pro, | 1.12 (1); |
| Gly, | 7.61 (7); | Ala, | 1.13 (1); | Val, | 2.08 (2); |
| Leu, | 2.00 (2); | Tyr, | 1.43 (1). | | |

Each of the tyrosylated C-peptides thus obtained is capable of being labeled by any known method because it includes a hydroxyphenyl group in the molecule. For example, the treatment with radioactive iodine in the presence of chloramine T followed by the termination of the reaction with sodium metabisulfite is employed for this purpose.

Process (5), Boc-Tyr[$^{125}$I]Tyr-Gly- human C-peptide

The tyrosylated C-peptide (2 μg) obtained in Process (4) is dissolved in 0.5 M phosphate buffer (pH, 7.5; 20 μl) and iodinated in the usual manner with Na$^{125}$I (2 m Ci) and chloramine T (20 μg) as an oxidizing agent at room temperature. After 30 sec, sodium metabisulfite (120 μg) is added to terminate the reaction.

The resultant Boc-Tyr($^{125}$I)-Gly- human C-peptide is fractionated by gel-filtration on a column of Sephadex G-25 (1×25 cm) with 0.1 M phosphate buffer (pH, 7.4) as eluant. Fractions (1 ml/tube) are collected and their radioactivities are measured. The tubes corresponding to a major peak are combined to give the title compound having a specific radioactivity of about 150 μci/μg.

Similar procedures are followed to obtain, Boc-[$^{125}$I]-Tyr-Gly-human C-peptide-(7-31) (specific radioactivity, 170 μCi/μg), Boc-Tyr($^{125}$I)-Gly- human C-peptide-(7-24) (200 μCi/μg) and Boc-[$^{125}$I]Tyr-Gly- human C-peptide-(7-21) (220 μCi/μg).

EXAMPLE

The measurement of C-peptide in serum samples by the use of the $^{125}$I-labeled derivative, obtained in the present invention, is performed, though it is rather conventional and described as a mere example, as follows.

C-Peptide-bovine serum albumin conjugate containing human C-peptide (normal 1-31; 1.25 mg) is dissolved in sterilized J.P. saline (1.25 ml) and to this solution is added complete Freund's adjuvant (1.25 ml) and the mixture is thoroughly emulsified by stirring. The emulsion is then injected intradermically into five (5) rabbits.

In the same manner the rabbits are injected with the C-peptide conjugate several (5–6) times at consecutive three (3) week intervals. The blood is collected ten (10) days after the last injection to obtain the desired antiserum.

Aside from the foregoing preparation of the antiserum, a standard C-peptide solution (100 μl), the prepared antiserum (100 μ, diluted to 1:25,000) and one of the labeled peptides obtained in Process 5) (40,000 cpm) are combined to stand at room temperature for about 20–24 hours to produce an antigen-antibody complex. To this is added a goat antirabbit IgG antibody (a conjugate of antibody with polyacrylamide gel, available from Bio-Rad Laboratories, U.S.A., under the trade name IMMUNOBEAD) and the mixture is allowed to stand at room temperature for one hour.

The mixture is then centrifuged to be removed of its supernatant by aspiration. Radioactivity of the sediments are counted with a scintillation counter.

DESCRIPTION OF THE DRAWING

Standard curves depicted in the attached drawing are dose-response curves obtained by measuring the radioactivities of the sediments in which the respective derivatives prepared in Process (5) are incorporated. $B_o$ represents the radioactivity bound to antibody in the absence of non-labeled C-peptide, while B represents the bound radioactivity in the presence of non-labeled C-peptide.

Same procedure as disclosed in connection with the plotting of the standard curves is followed in actual measurement of C-peptide in serum sample to be determined, which, in this case, is substituted for the standard C-peptide solution. The concentration of the C-peptide in the serum sample is read off the standard curves.

Alternatively, the serum sample may be combined with the antiserum and one of the labeled C-peptides and then incubated at 4° C. for 48 hours. The incubated mixture is then treated with a conventional double antibody method and the radioactivity of the sediments is counted.

Any one skilled in the art will have other modifications occur to him based on the teachings of the present invention. These modifications are intended to be encompassed within the scope of this invention.

What is claimed is:

1. A proinsulin C-peptide derivitive of the formula:

Y-Tyr-Gly-R wherein Y represents a hydrogen atom or an amino protecting group, Tyr represents a tyrosine residue, wherein at least one of the hydrogen atoms on the phenyl ring may be substituted by a radioactive iodine, Gly represents a glycine residue, and R represents a peptide residue corresponding to an amino acid sequence which includes at least positions 7–21 of human proinsulin C-peptide.

2. A proinsulin C-peptide derivative as claimed in claim 1, wherein R represents an amino acid sequence selected from the group consisting of:
   human proinsulin C-peptide (positions 1 through 31), a peptide corresponding to positions 7 through 31 of, a peptide corresponding to positions 7 through 24 of, and a peptide corresponding to positions 7 through 21 of human proinsulin C-peptide.

3. A proinsulin C-peptide derivative as claimed in claim 2, wherein R is human proinsulin C-peptide (positions 1 through 31).

4. A proinsulin C-peptide derivative as claimed in claim 2, wherein R is a peptide which corresponds to positions 7 through 31 of human proinsulin C-peptide.

5. A proinsulin C-peptide derivative as claimed in claim 2, wherein R is a peptide which corresponds to positions 7 through 24 of human proinsulin C-peptide.

6. A proinsulin C-peptide derivative as claimed in claim 2, wherein R is a peptide which corresponds to positions 7 through 21 of human proinsulin C-peptide.

7. A proinsulin C-peptide derivative as claimed in any one of the preceding claims, wherein Y is a tertiary butoxycarbonyl group.

8. A proinsulin C-peptide derivative as claimed in claim 7, wherein at least one of the hydrogen atoms in the phenyl ring nucleus of the tyrosine residue is substituted by iodine 125 ($^{125}I$).

9. An agent for determining the proinsulin C-peptide level in serum comprising a proinsulin C-peptide derivitive of the formula:

Y-Tyr-Gly-R wherein Y represents a hydrogen atom or an amino protecting group, Tyr represents a tyrosine residue wherein at least one of the hydrogen atoms on the phenyl ring may be substituted by a radioactive iodine, Gly represents a glycine residue, and R represents a peptide residue corresponding to an amino acid sequence which includes at least positions 7–21 of human proinsulin C-peptide.

* * * * *